United States Patent [19]
Jesion et al.

[11] Patent Number: 5,636,135
[45] Date of Patent: Jun. 3, 1997

[54] METHOD AND APPARATUS FOR TIME-ALIGNMENT OF NON-PLUG FLOW

[75] Inventors: Gerald Jesion, Woodhaven; Lee A. Feldkamp, Plymouth; Gintaras V. Puskorius, Redford; Christine A. Gierdzak, Grosse Ile; James W. Butler, Livonia, all of Mich.

[73] Assignee: Ford Motor Company, Dearborn, Mich.

[21] Appl. No.: 523,318

[22] Filed: Sep. 5, 1995

[51] Int. Cl.⁶ .......................... G01N 21/84; G06F 17/10
[52] U.S. Cl. .......................... 364/497; 73/23.37; 395/911
[58] Field of Search ........................ 364/497, 498, 364/554, 581; 73/23.24, 23.37; 395/924, 911

[56] References Cited

U.S. PATENT DOCUMENTS

| | | | |
|---|---|---|---|
| 4,059,994 | 11/1977 | Annino et al. | 73/23.1 |
| 4,801,805 | 1/1989 | Butler et al. | 250/343 |
| 4,881,183 | 11/1989 | Groe | 364/498 |
| 4,922,362 | 5/1990 | Miller et al. | 367/46 |
| 4,928,015 | 5/1990 | Butler et al. | 250/343 |
| 5,113,367 | 5/1992 | Marrian et al. | 364/819 |
| 5,175,678 | 12/1992 | Frerichs et al. | 364/148 |
| 5,181,171 | 1/1993 | McCormack et al. | 364/421 |
| 5,239,483 | 8/1993 | Weir | 364/497 |
| 5,249,954 | 10/1993 | Allen et al. | 431/14 |
| 5,255,512 | 10/1993 | Hamburg et al. | 60/274 |
| 5,272,621 | 12/1993 | Aoki | 364/164 |
| 5,311,445 | 5/1994 | White | 364/498 |
| 5,313,406 | 5/1994 | Kauppinen et al. | 364/498 |
| 5,585,919 | 12/1996 | Kurtzberg et al. | 364/495 |

Primary Examiner—Emanuel T. Voeltz
Assistant Examiner—Kyle J. Choi
Attorney, Agent, or Firm—Richard D. Dixon

[57] ABSTRACT

A method of time-aligning sequential gas concentrations, generated by a non-plug flow real time emissions analyzer, with corresponding plug flow inputs from an emissions source includes selecting a sequence of known plug flow test gas pulses representative of the emissions source, feeding the known plug flow test gas pulses into the analyzer, saving a sequence of blurred test pulses generated by the analyzer, determining a mathematical relationship between the known plug flow test gas pulses and the blurred test pulses, configuring a filter such that the filter corresponds to the mathematical relationship, inputting a subset of the blurred test pulses into the filter, recording a sequence of deconvoluted test pulses generated by the filter, comparing the deconvoluted test pulses with a subset of the known plug flow test gas pulses to generate difference errors, adjusting the filter to minimize the plurality of difference errors, repeating the first inputting step, the first recording step, the comparing step, and the adjusting step to reduce the difference errors, feeding the plug flow inputs into the analyzer, recording the sequential gas concentrations generated by the analyzer, and deconvoluting the sequential gas concentrations.

8 Claims, 4 Drawing Sheets

METHOD AND APPARATUS FOR TIME-ALIGNMENT OF NON-PLUG FLOW

FIELD OF THE INVENTION

The present invention relates to non-plug flow analyzers, and, more particularly, to providing enhanced time alignment of measured flow concentrations for improved transient analysis.

DESCRIPTION OF THE RELATED ART

Vehicle emissions have been an object of increasing interest in recent years. Government and industry have devised a number of emissions standards and specific, rigid operational tests for measuring the concentration of particular gases in vehicle exhaust. Historically, most of these tests have included a variety of vehicle operating conditions, such as idling, accelerating, decelerating, and moving at a constant, non-zero velocity. Test results have traditionally been expressed as a figure of the total mass emissions for each gas of interest emitted over the entire course of the test, in units of grams or grams per mile. Furthermore, since total mass emissions is the product of the gas flow rate times the gas concentration, total mass emissions could also be theoretically computed by summing the incremental products of the incremental gas flow rates and the corresponding incremental gas concentrations throughout the duration of the test.

While total mass emissions have hitherto been adequate for comparison purposes, the variety of vehicle operating modes during testing makes it difficult to isolate specific instances of greater or lesser emissions and associate them with specific modes of operation, known as modal analysis. In particular, it would be desirable to examine the concentration of a specific gas and its corresponding flow rate under specific test conditions, such as, for example, acceleration, to pinpoint those vehicle operating modes which most significantly contribute to the vehicle's total emissions.

Gas flow rates have generally been measured with a reasonable degree of success, but it has proven much more difficult to measure the corresponding incremental gas concentrations associated with a particular flow. This is because the measurement of gas concentration is hindered by the natural tendency of gases to mix when introduced into a fixed volume test cell, a problem which is characteristic of non-plug flow. This mixing blurs the time alignment between a specific gas concentration and the corresponding gas flow, making it difficult to properly correlate the two so that an actual emission figure can be determined. Additionally, it is difficult to precisely determine the actual quantity of gas present at a particular point in time, which is known as transient analysis, because the measuring equipment must wait for a substantial time period to measure the concentration, potentially permitting the gas to disperse within the test fixture.

For example, methods for measuring gas emissions are detailed in U.S. Pat. No. 4,801,805, "Method of Measuring Multicomponent Constituency of Gas Emission Flow" and U.S. Pat. No. 4,928,015, "Measuring Multicomponent Constituency of Gas Emission Flow." In particular, these methods utilize non-plug flow Real Time Emissions Analyzers (REAs) with Fourier-transform, infrared spectrometers (FTIRs) which pass light through a test cell containing emissions gas. While such fixtures are adequate for determining total test emissions and assessing intermediate emissions trends, it would be desirable to have an improved system which provides better time resolution for improved transient analysis of emissions and greater precision in time-aligning gas concentrations with their corresponding gas flows. This is the aim of the present invention.

SUMMARY OF THE INVENTION

A method of time-aligning sequential gas concentrations, generated by a non-plug flow real time emissions analyzer, with corresponding plug flow inputs from an emissions source includes selecting a sequence of known plug flow test gas pulses representative of the emissions source, feeding the known plug flow test gas pulses into the analyzer, saving a sequence of blurred test pulses generated by the analyzer, determining a mathematical relationship between the known plug flow test gas pulses and the blurred test pulses, configuring a filter such that the filter corresponds to the mathematical relationship, inputting a subset of the blurred test pulses into the filter, recording a sequence of deconvoluted test pulses generated by the filter, comparing the deconvoluted test pulses with a subset of the known plug flow test gas pulses to generate difference errors, adjusting the filter to minimize the plurality of difference errors, repeating the first inputting step, the first recording step, the comparing step, and the adjusting step to reduce the difference errors, feeding the plug flow inputs into the analyzer, recording the sequential gas concentrations generated by the analyzer, and deconvoluting the sequential gas concentrations.

A primary object of the present invention is to provide a new and improved method of measuring transient emissions concentrations. More specifically, it is an object of the present invention to time-align transient emissions concentrations with their corresponding total flow rates. A primary advantage of this invention is that it permits transient analysis of emissions concentrations during vehicle emissions testing. An additional advantage is that it permits more accurate calculation of mass emission rates. A further advantage is that it can be customized to deconvolute data from a variety of real time emissions analyzers with varying degrees of skew.

Other objects, features, and advantages will be apparent from a study of the following written description and drawings.

DETAILED DESCRIPTION OF THE PREFERRED EMBODIMENTS

Figure 1:
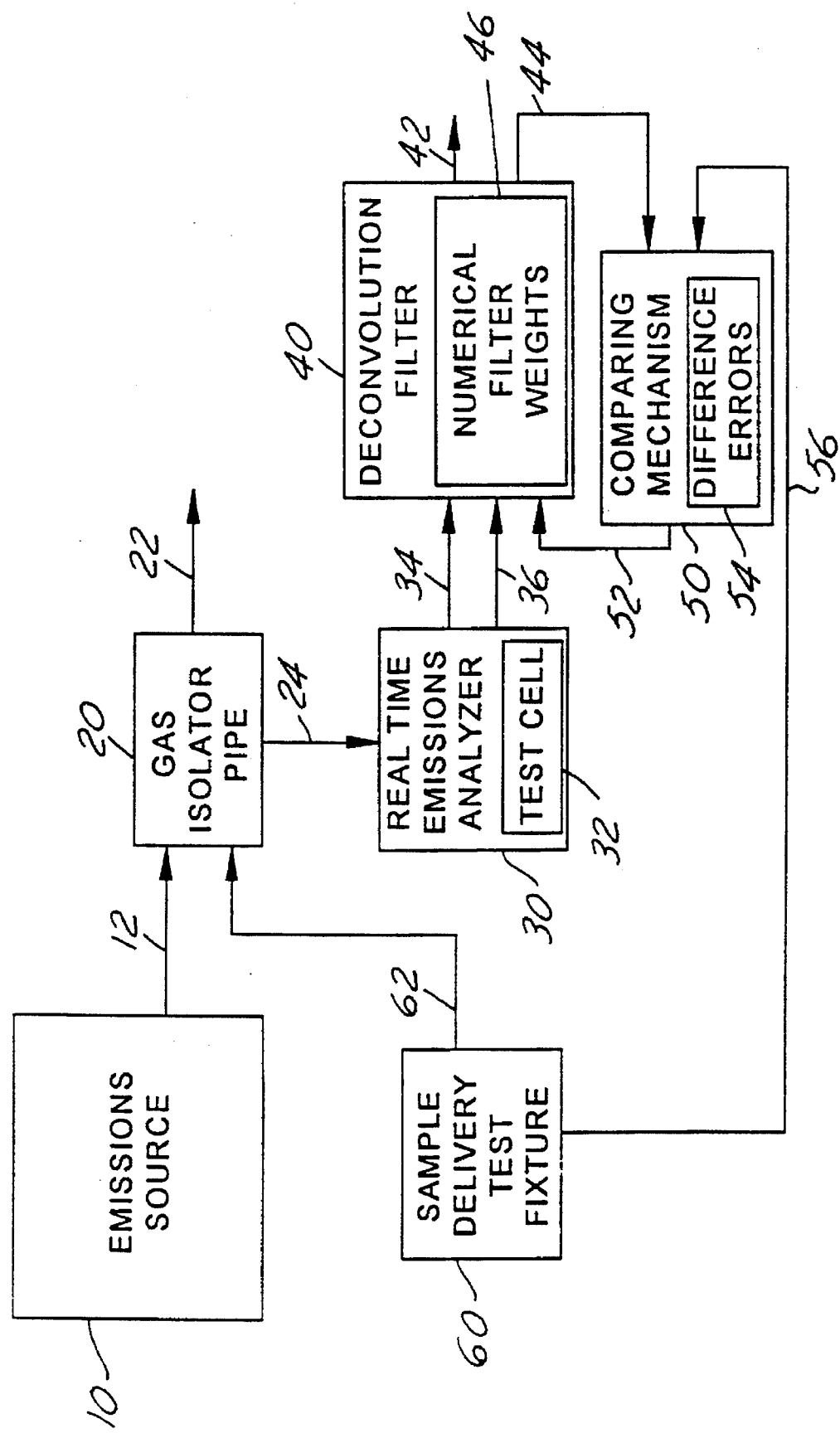
FIG. 1 is a block diagram of an emissions measuring system according to the present invention.

Referring now to FIG. 1, a block diagram of an emissions measuring system includes an emissions source 10, such as, for example, an automobile tail pipe. Emissions 12 from source 10 are received by a gas isolator pipe 20, which draws off a representative emissions sample 24 for analysis. Note that at this point sample 24 is a plug flow. The remaining emissions 22 are discarded. Note that the emissions 12 may contain a number of gases to be analyzed, including, for example, carbon dioxide ($CO_2$), carbon monoxide (CO), hydrocarbons (HC) and oxides of nitrogen ($NO_x$). Representative emissions sample 24 is received by a non-plug flow Real Time Emissions Analyzer 30 (REA). REA 30 includes a Fourier-Transform infrared spectrometer (FTIR) system having a test cell 32. Since test cell 32 is essentially a fixed volume container, representative emissions sample 24 mixes with the gas present in the test cell, causing the specific concentration of emissions at a particular instant in time to become blurred. Representative emissions sample 24 thus becomes a flow of the non-plug type upon entering test cell 32, and is thereafter referred to as a non-plug flow.

REA 30 measures the gas concentrations throughout the pendency of the test, generating blurred sequential gas concentrations 34. Sequential gas concentrations 34 are received by a deconvolution filter 40, which deconvolutes them into time-aligned gas concentrations 42. Filter 40 is comprised of a series of numerical filter weights 46. These weights are multiplied with inputs to the filter generated by the REA to create a sequence of time-aligned gas concentrations. For example, in a preferred embodiment, filter 40 is a linear filter of the form $$y(k) = \sum_{j=k}^{k+n-1} W(j-k+1) \cdot x(j)$$

where y(k) is the filter output at time k, x(j) is the REA measurement at time step j, and each W(j−k+1) is one of the numerical filter weights 46. In a preferred embodiment, there are twenty-five filter weights, so n equals 25 in the above equation.

The numerical values for the filter weights are established by a training process. In the training process, a sequence of known plug flow test gas pulses 62 is selected which are believed to be representative of the range of flows and concentrations which the actual emissions source 10 typically generates. Note that the specific gas selected for the test gas may be any of those gases typically of interest in emissions testing. Known plug flow test gas pulses 62 are generated by a sample delivery test fixture 60 and fed into gas isolator pipe 20, in place of emissions source 10. After passing through test cell 32 of REA 30, the resulting sequence of blurred test pulses 36 from REA 30 are fed into deconvolution filter 40, whose numerical filter weights 46 have been initialized to nominal random values. For example, in a preferred embodiment using a linear filter, the twenty-five numerical weights are all set to randomly selected values from the range, for example, of +/−0.1. Deconvolution filter 40 generates deconvoluted test pulses 44, which are compared to known plug flow test gas pulse characteristics 56 by a comparing mechanism 50 to generate a series of difference errors 54. Comparing mechanism 50 analyzes the difference errors 54 and makes adjustments 52 to numerical filter weights 46 to minimize difference errors 54. Note that various methods of calculating difference errors and making weight adjustments can be used, depending on the complexity of the filter and the desired degree of accuracy. Such methods include least-mean-squares (LMS), recursive-least-squares (RLS), decoupled extended Kalman filter (DEKF), standard back propagation (SBP), or other known methods. For example, in a preferred embodiment using a linear filter, an RLS training algorithm is used.

Using the adjusted weights, deconvolution filter 40 re-evaluates blurred test gas pulses 36 from REA 30, generating a new set of deconvoluted test pulses 44. Comparing mechanism 50 analyzes these new deconvoluted test pulses 44 against known plug flow test gas pulses 56 and makes additional weight adjustments 52. This cycle repeats until the difference errors are minimized to an acceptable level. For example, in a preferred embodiment using a linear filter and the RLS training algorithm, approximately one hundred iterations were performed.

Once deconvolution filter 40 has been successfully trained, it is employed in the manner previously described to analyze the actual emissions from the emissions source to be tested. Note that once the deconvolution filter is trained to compensate for a particular REA, it may be used to deconvolute any of the emissions gases measured by that REA, and need not be trained separately for each gas to be deconvoluted.

Figure 2:
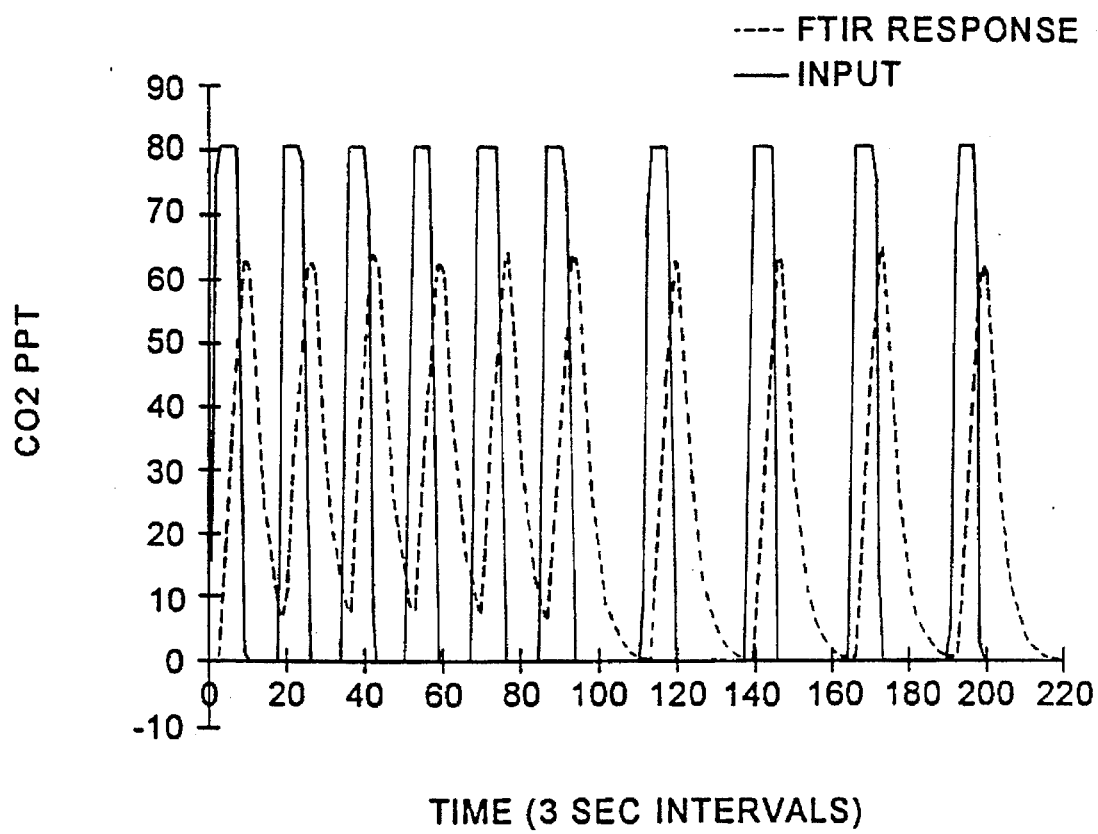
FIG. 2 is a graph of REA input versus REA output illustrating an example of the problem of blurred data addressed by the present invention.

Referring now to FIG. 2, a graph of REA input versus REA output illustrates one example of the problem of blurred data addressed by the present invention. The horizontal axis reflects three-second time intervals, and the vertical axis represents an emissions flow of carbon dioxide ($CO_2$) in parts per thousand. The solid line shows a series of known plug flow test gas pulses of $CO_2$, and the dotted line shows the corresponding output measurements of this input performed by the REA's FTIR.

From the graph it can be seen that the FTIR response to the input waveform significantly lags the actual input in time. This lag has three distinct effects. First, as illustrated by the earlier pulses, which are of greater frequency, the time lag of the response prevents it from returning to zero between pulses. Consequently, the overlapping effect of the pulses on the output makes it difficult to separate the effects of adjacent input pulses.

Second, the lag between input and output makes it difficult to time-align the input concentrations with their respective flow rates, so that mass emissions may be computed. For example, the final pulse on the graph illustrates that while the input pulse ceased at interval 200, the final effects of this pulse were dissipated much later, at interval 220. The consequence of this lag in the present example is that the effect of a particular input interval is scattered over an area of twenty intervals. Thus, when computing, for example, the concentration of the input at time interval 199, the REA must somehow account for that portion of the input which is reflected at each of the intervals from 199 to 219. This suggests that the output at any particular interval is a function of the sum of at least twenty subsequent inputs, which is useful for determining a number of filter terms, or weights, which are needed to deconvolute this blurred data. Allowing, for example, five additional samples for extra margin, this suggests that for the given example, twenty-five filter terms should suffice to deconvolute the data for this specific application. Note that other applications might require greater or fewer terms, depending on the characteristics of the specific flow.

The third effect of the lag is reflected in the FTIR's failure to peak as high as the input, falling short in this example by approximately 17 parts per thousand. This, too, is a result of the spreading effect. Note that while the total area under each of the waveforms is approximately equal, the dotted waveform tends to spread this area more evenly than the solid waveform. The consequence is that while the total emissions can be accurately computed (because it is based on the area under the waveform), the transient emissions at any interval are somewhat inaccurate, owing to the effects of the lag. This graph thus illustrates the specific problems which are addressed by the present invention.

Figure 3:
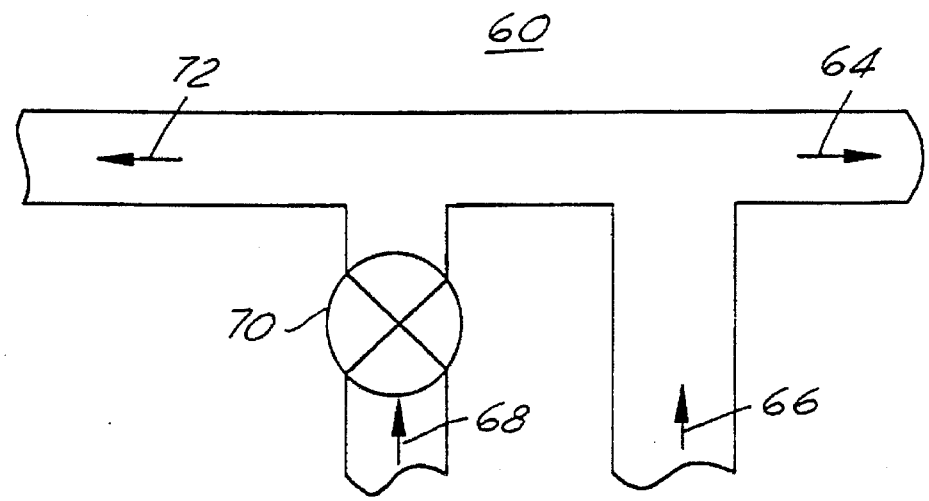
FIG. 3 is a diagram of a test fixture for providing known plug flow pulses of test gas according to the present invention.

Referring now to FIG. 3, the details of sample delivery test fixture 60 for providing known plug flow test gas pulses to the REA for use in training the deconvolution filter are shown. Fixture 60 is initially filled with a gas, such as, for example, nitrogen ($N_2$), which is provided as indicated by arrow 66. A test gas, such as, for example, carbon dioxide ($CO_2$), is provided into fixture 60 as indicated by arrow 68. Note that other gases could be used in place of the nitrogen and carbon dioxide. In general, it is preferable to use a gas which is typical of those emissions to be measured, in a concentration whose range is within the anticipated range of concentration of the actual emissions, within a gas which is typical of those likely to be used in test cell 32. An electric valve 70 is used to control timing and concentration of the test pulses which are provided to the REA through the fixture as indicated by arrow 72 at a flow rate of, for example, 3 liters per minute. Note that excess gas which is not needed for testing purposes, including both nitrogen and carbon dioxide in this example, is discharged to the atmosphere as indicated by arrow 64.

Figure 4:
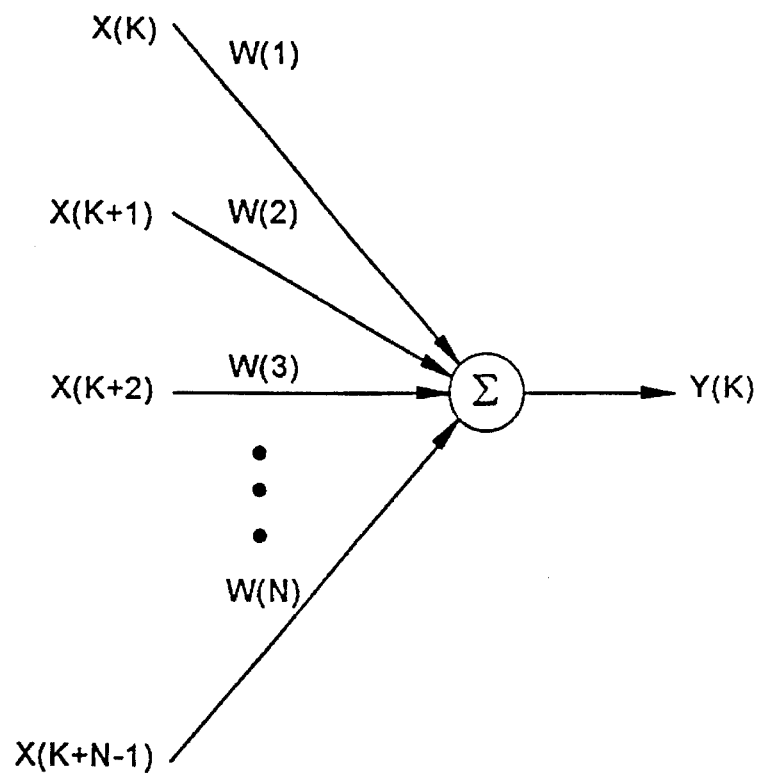
FIG. 4 is a graph showing a filter equation for a preferred embodiment of the present invention.

Referring now to FIG. 4, a generalized filter equation for a preferred embodiment of the present invention shows a simple linear filter with n filter weights 46. On the right side, y(k) represents the time-aligned gas concentration 42 at a particular time interval k, which is generated by deconvolution filter 40. On the left side, x(k) represents the blurred output of the REA analyzer which is provided to deconvolution filter 40 as input at the particular time interval k. Similarly, x(k+1) represents the input at time interval (k+1), and so forth. In the middle are the numerical filter weights 46, numbered w(1) through w(n), where n represents the number of filter terms required, as discussed previously with FIG. 2. For the simple linear filter of a preferred embodiment, y(k) is shown as the sum of the products of a series of present and future inputs each multiplied by a corresponding filter weight. Thus, for a preferred embodiment, the contribution of a future input towards the measurement of the present input is determined by the value of the filter weight with which it is multiplied.

Figure 5:
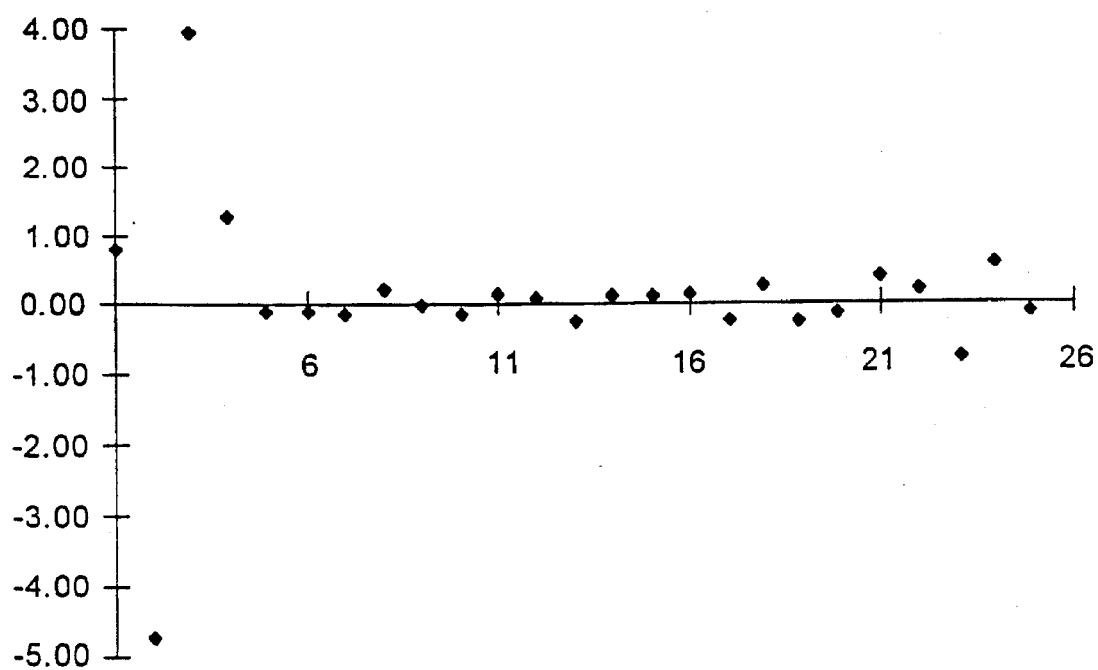
FIG. 5 is a graph of numerical filter weights for a preferred embodiment of the present invention.

Referring now to FIG. 5, a graph of numerical filter weights 46 for a preferred embodiment of the present invention shows the variety of numerical weight values for a sample filter according to the present invention. The horizontal axis represents the various filter weights by term number n, where n ranges from 1 to 25. The vertical axis represents a numerical weight value, which in a preferred embodiment is multiplied with a particular input sample.

For example, filter coefficient one on the diagram has a weight value of approximately 0.85, while filter coefficient two has a value of approximately −4.8, filter coefficient three has a value of approximately 4.2, and filter coefficient twenty-five has a value of approximately −0.15. For a specific time interval k of, for example, 127, the deconvoluted output at time 127 would be the sum of twenty-five products: 0.8 multiplied with the input at time 127, plus −4.8 multiplied with the input at time 128, plus 4.2 multiplied with the input at time 129, and so forth, with the final addend of the sum being −0.15 multiplied with the input at time 151. In this fashion the lag problems discussed with FIG. 2 are thus corrected, and the deconvoluted output waveform is restored to resemble the original input waveform in both time and magnitude.

Figure 6:
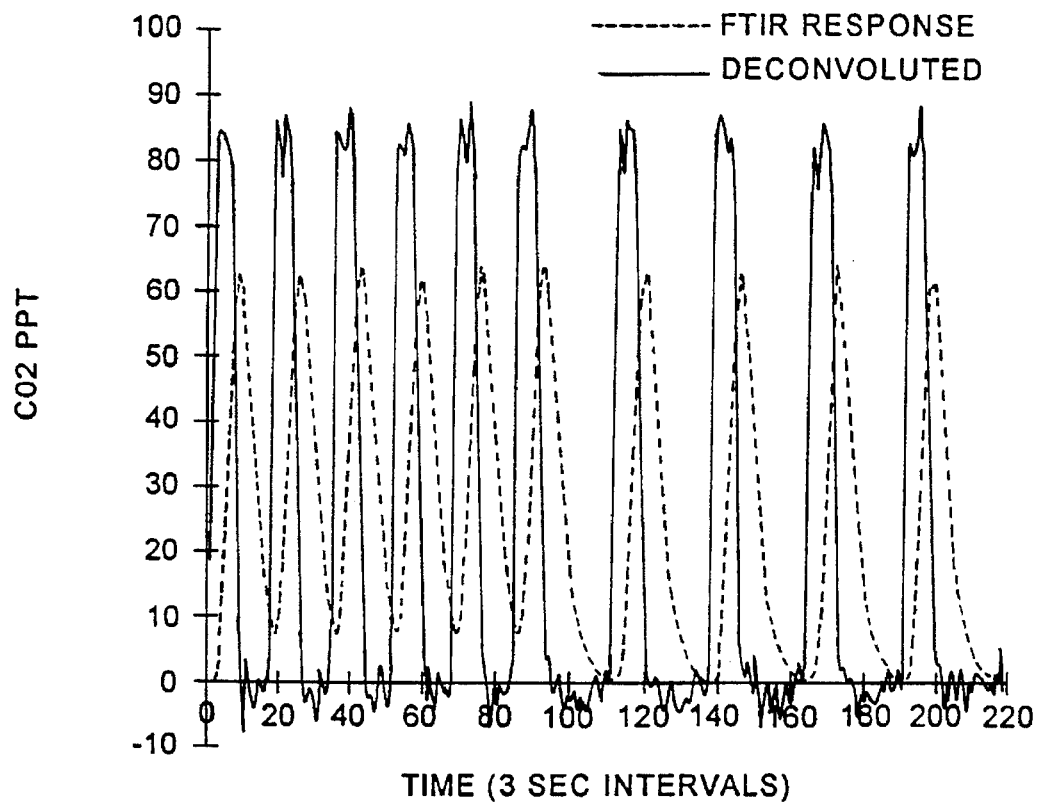
FIG. 6 is a graph showing REA output and its deconvolution according to the present invention.

Referring now to FIG. 6, a graph shows REA output and the subsequent deconvolution by the filter 40 for one sample embodiment of the present invention. The horizontal axis reflects three-second time intervals, and the vertical axis represents an emissions flow of carbon dioxide ($CO_2$) in parts per thousand. The dotted line shows the measurements of a series of known plug flow test gas pulses 62 of $CO_2$ performed by the REA's FTIR. The solid line shows the deconvolution of this data by the deconvolution filter 40. When compared with the original input test pulses of FIG. 2, the deconvoluted waveform of FIG. 6 is seen to be much closer in time and magnitude than the REA's FTIR output. Note that the filter emphasizes noise present in the data. This is most clearly noted at the peaks and valleys of the deconvoluted waveform of FIG. 6. This noise could be filtered out if desired, but the resulting waveform might lose some of its accuracy with respect to time and magnitude. In a preferred embodiment it is left unaltered, in order to minimize the effects of the REA's FTIR lag. Note that although this graph illustrates the results of applying a sequence of known plug flow test gas pulses specifically chosen to properly train the filter, it should provide a similar degree of accuracy when measuring emissions from an actual emissions source, provided that the selected test pulses were, in fact, representative of the full range of anticipated input data from the actual emissions source.

Figure 7:
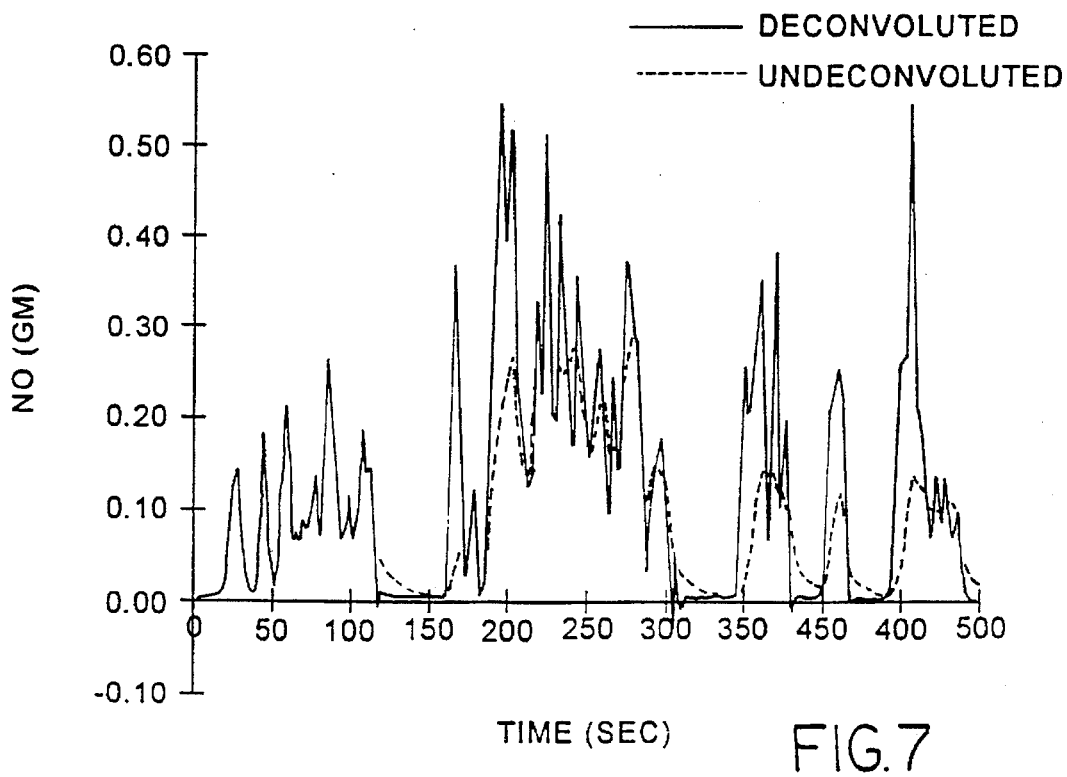
FIG. 7 is a graph illustrating transient mass emissions computed according to REA concentrations alone and transient mass emissions as determined according to the present invention.

Finally, referring to FIG. 7, a graph illustrates an example of the difference between transient mass emissions computed according to REA gas concentrations alone and transient mass emissions as determined according to the present invention. This data is from an actual emissions source and reflects the varying quantity of a particular gas emitted by a vehicle during a test cycle. The horizontal axis shows time in seconds, while the vertical axis shows mass emissions in grams of nitric oxide (NO), which are computed by multiplying the deconvoluted gas concentrations times the actual flow rate of the gas. Note that the mass emissions computed from the REA output data, labeled undeconvoluted, is shown by the dotted line, while the mass emissions computed from the deconvolution of the REA output data is labeled deconvoluted and shown by the solid line.

The graph illustrates the effect of time-aligned concentrations on the total mass emissions at specific time intervals, and demonstrates the impact of the present invention in determining transient mass emissions. For example, at approximately 160, 190, 360 and 450 seconds there are significant peaks in the deconvoluted waveform which were largely missed by the blurred REA output. These peaks may be indicative of significant changes in the operating mode of the vehicle under test and thus may suggest specific focus areas for further reducing emissions. With proper time-alignment, their presence becomes readily apparent and permits the corresponding operating modes of the vehicle to be readily identified. Note that the areas under the original and corrected curves are not the same, giving rise to different total mass emissions. This is a consequence of the time varying flow of the gas.

From the foregoing description, one ordinarily skilled in the art can easily ascertain the essential characteristics of this invention and, without departing from the spirit and scope of the claims, can make various changes and modifications to the invention to adapt it to various uses and conditions.

We claim:

1. A method of time-aligning a plurality of sequential gas concentrations, generated by a non-plug flow real time emissions analyzer, with a plurality of corresponding plug flow inputs from an emissions source, comprising the steps of:

selecting a sequence of known plug flow test gas pulses representative of the emissions source;

feeding the sequence of known plug flow test gas pulses into the non-plug flow real time emissions analyzer;

saving a sequence of blurred test pulses generated by the non-plug flow real time emissions analyzer;

determining a mathematical relationship between the sequence of known plug flow test gas pulses and the sequence of blurred test pulses;

configuring a filter corresponding to the mathematical relationship, the filter including a plurality of numerical filter weights having random initial values;

inputting a subset of the sequence of blurred test pulses into the filter;

recording a sequence of deconvoluted test pulses generated by the filter;

comparing the deconvoluted test pulses with a subset of the sequence of known plug flow test gas pulses to generate a plurality of difference errors, the subset of the sequence of blurred test pulses corresponding to and originating from the subset of the sequence of known plug flow test gas pulses;

adjusting the filter weights to minimize the plurality of difference errors;

repeating said first inputting step, said first recording step, said comparing step, and said adjusting step to reduce the plurality of difference errors;

feeding the plug flow inputs into the non-plug flow real time emissions analyzer;

recording the plurality of sequential gas concentrations generated by the non-plug flow real time emissions analyzer; and deconvoluting the plurality of sequential gas concentrations.

2. An apparatus for deconvoluting a plurality of blurred sequential gas concentrations generated by a non-plug flow real time emissions analyzer for a non-plug gas flow in a test cell, comprising:

a sample delivery test fixture, coupled to the non-plug flow real time emissions analyzer, said sample delivery test fixture providing a sequence of known plug flow test gas pulses to the non-plug flow real time emissions analyzer;

an adjustable filter, coupled to the non-plug flow real time emissions analyzer, for filtering the plurality of blurred sequential gas concentrations into a plurality of time-aligned gas concentrations; and adjusting means, coupled to said adjustable filter and to said sample delivery test fixture, for adjusting said adjustable filter according to a plurality of differences between the sequence of known plug flow test gas pulses and the plurality of time-aligned gas concentrations.

3. An apparatus according to claim 2, said adjustable filter further comprising a plurality of adjustable filter weights.

4. An apparatus according to claim 3, said adjusting means further comprising a comparator for comparing the deconvoluted test pulses with the subset of the sequence of known plug flow test gas pulses, generating means for generating a plurality of difference errors reflecting differences between the deconvoluted test pulses and the subset of the sequence of known plug flow test gas pulses, and converting means for converting the plurality of difference errors into a plurality of adjustments to the filter weights to reduce the plurality of difference errors.

5. An apparatus according to claim 2, said adjusting means further comprising a decoupled extended Kalman filter.

6. An apparatus according to claim 2, said adjusting means further comprising a recursive least squares filter.

7. An apparatus according to claim 2, said adjustable filter further comprising a linear filter.

8. An apparatus according to claim 2, wherein said adjustable filter is a neural network.

* * * * *